US00PP22664P2

(12) United States Plant Patent
Klemm et al.

(10) Patent No.: US PP22,664 P2
(45) Date of Patent: Apr. 17, 2012

(54) ***PELARGONIUM* PLANT NAMED 'KLEPZ10271'**

(50) Latin Name: *Pelargonium zonale*
Varietal Denomination: KLEPZ10271

(75) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 13/065,568

(22) Filed: Mar. 24, 2011

(51) Int. Cl.
*A01H 5/00* (2006.01)

(52) U.S. Cl. ..... Plt./326

(58) Field of Classification Search ..... Plt./326
See application file for complete search history.

*Primary Examiner* — June Hwu
*Assistant Examiner* — Louanne Krawczewicz Myers
(74) *Attorney, Agent, or Firm* — Jondle & Associates, P.C.

(57) ABSTRACT

A new variety of *Pelargonium* named 'KLEPZ10271', particularly characterized by greenish white flowers, medium green foliage, medium growth habit, good branching, and easy, rich flowering, is disclosed.

1 Drawing Sheet

Genus and species: *Pelargonium zonale.*
Variety denomination: 'KLEPZ10271'.

BACKGROUND OF THE NEW PLANT

The present invention comprises a new and distinct variety of *Pelargonium,* botanically known as *Pelargonium zonale,* and hereinafter referred to by the variety name 'KLEPZ10271'. The new variety is the result of a controlled cross conducted in June 2005 in Kenya between the proprietary female *Pelargonium* parent, 'PZ 04 0112' (unpatented), and the proprietary male *Pelargonium* parent, 'KLEP01052' (U.S. Plant Pat. No. 13,202). A single plant selection was subsequently chosen for further evaluation and asexual propagation.

The new variety was first propagated via vegetative cuttings in September 2006 in Stuttgart, Germany and has been asexually reproduced repeatedly by vegetative cuttings in Stuttgart, Germany for approximately five to six generations. 'KLEPZ10271' has been found to retain its distinctive characteristics through successive asexual propagations via vegetative cuttings.

Plant Breeder's Rights for this variety were applied for in the following countries: Canada on Mar. 19, 2010, Switzerland on Jun. 29, 2010, the European Union on Jul. 9, 2010, and Norway on Sep. 15, 2010. 'KLEPZ10271' has not been made publicly available or sold more than one year prior to the filing date of this application.

SUMMARY OF THE INVENTION

The following are the most outstanding and distinguishing characteristics of this new variety when grown under normal horticultural practices in a glass greenhouse in Stuttgart, Germany.

1. Greenish white flowers;
2. Medium green foliage;
3. Medium growth habit;

4. Good branching; and
5. Easy, rich flowering.

DESCRIPTION OF THE PHOTOGRAPH

This new *Pelargonium* plant is illustrated by the accompanying photograph which shows blooms, buds, and foliage of the plant. The colors shown are as true as can be reasonably obtained by conventional photographic procedures.

The photograph is of a 3-month old plant taken in Spring 2010 grown from a rooted cutting in a 12 centimeter pot in a glass greenhouse in Stuttgart, Germany under conditions which approximate those generally used in normal horticultural practice.

DESCRIPTION OF THE NEW VARIETY

The following detailed descriptions set forth the distinctive characteristics of 'KLEPZ10271'. The data which define these characteristics were collected from asexual reproductions carried out in Stuttgart, Germany. The plant history was taken on 3-month old, un-pinched plants grown in 12 centimeter pots in a glass greenhouse in Stuttgart, Germany. The color readings were determined under natural light. Color references are to The R.H.S. Colour Chart of The Royal Horticultural Society of London (R.H.S.), Fifth Edition (2007).

DETAILED BOTANICAL DESCRIPTION OF THE NEW PLANT

Classification:
*Family.*—Geraniaceae.
*Species.*—*Pelargonium zonale.*
*Common name.*—*Pelargonium* (Geranium).
*Denomination.*—'KLEPZ10271'.

Parentage:
*Female parent.*—The proprietary female *Pelargonium* parent, 'PZ 04 0112' (unpatented).
*Male parent.*—The proprietary male *Pelargonium* parent, 'KLEP01052' (U.S. Plant Pat. No. 13,202).

Plant:
*Habit*.—Medium, upright.
*Height to the top of the umbels*.—22.0 cm to 25.0 cm.
*Spread*.—28.0 cm to 30.0 cm.
*Life cycle*.—Spring to Fall.
*Form*.—Round, bushy.
*Time to produce a rooted cutting*.—18 days.
*Time to bloom from propagation*.—105 days.
*Lastingness of inflorescence on the plant*.—14 days.
Stems:
*Stem color*.—RHS 137C.
*Pubescence*.—Yes, short.
*Stem form*.—Upright, erect.
*Diameter*.—0.5 cm to 0.8 cm.
*Length*.—10.0 cm to 15.0 cm.
*Internode length*.—0.8 cm to 1.5 cm.
Leaves:
*Arrangement*.—Alternate.
*Shape*.—Kidney-shaped, round.
*Apex*.—Round.
*Base*.—Open.
*Margin*.—Crenated.
*Surface texture* (*both upper and lower surfaces*).—Dull.
*Length*.—6.0 cm to 7.0 cm.
*Width*.—6.0 cm to 7.0 cm.
*Color*.—Upper surface: RHS 137B. Lower surface: RHS 137C.
*Fragrance*.—Absent.
*Surface pubescence*.—Absent.
*Petiole*.—Length: 4.0 cm to 6.0 cm. Diameter: 0.2 cm. Color: RHS 137C.
*Venation pattern*.—Palmate.
*Venation color*.—Upper surface: RHS 139C. Lower surface: RHS 139D.
*Zonation*.—Absent.
Inflorescence:
*Flowering habit*.—Continuously.
*Umbels*.—Length: 6.0 cm to 8.0 cm. Diameter: 7.0 cm to 9.0 cm.
*Individual florets of the umbel*.—Depth: 1.5 cm. Diameter: 3.0 cm.
*Flowers per umbel*.—10 to 20.
*Umbels per plant*.—3 to 5.
*Fragrance*.—Absent.
Flower buds:
*Cluster shape*.—Round.
*Cluster size*.—Length: 4.0 cm. Width: 4.0 cm.
*Buds per cluster*.—10 to 20.
*Bud*.—Length: 0.6 cm. Diameter: 0.4 cm. Shape: Ovate. Apex: Peaked. Base: Obtuse. Margin: Plane. Color: RHS 137B.
*Corolla*.—Diameter: 3.0 cm. Depth: 1.5 cm.
Petals:
*Quantity per flower*.—6 to 9 and petaloids.
*Shape*.—Spatulate.
*Apex*.—Round, entire.
*Base*.—Obtuse.
*Margin*.—Entire.
*Length*.—1.5 cm to 2.0 cm.
*Width*.—1.4 cm to 1.6 cm.
*Texture* (*both upper and lower surfaces*).—Smooth.
*Color of lobes*.—Upper and lower lobes (both upper and lower surfaces): RHS NN155A and RHS 157C.
*Corolla tube color*.—Inner and outer surface: RHS NN155A and RHS 157C.
*Fragrance*.—Absent.
Sepals:
*Number per flower*.—5.
*Shape*.—Elliptic.
*Apex*.—Peaked.
*Base*.—Obtuse.
*Margin*.—Entire.
*Color*.—Upper surface: RHS 137B. Lower surface: RHS 139D.
*Length*.—0.9 cm.
*Width*.—0.2 cm.
Pedicel:
*Length*.—1.5 cm.
*Diameter*.—0.15 cm.
*Color*.—RHS 137C.
*Texture*.—Rough.
Peduncle:
*Length*.—9.0 cm to 12.0 cm.
*Diameter*.—0.4 cm to 0.5 cm.
*Color*.—RHS 137C.
*Texture*.—Rough.
Reproductive organs:
*Stamens*.—Number: Approximately 5. Anther length: 0.15 cm. Filament length: 0.5 cm. Filament color: RHS NN155D. Pollen amount: Moderate. Pollen color: RHS 28D.
*Pistils*.—Number: 1. Stigma color: RHS N155. Style length: 0.3 cm. Style color: RHS N155. Ovary arrangement: One upright. Ovary color: RHS 139D.
Disease, pest, and stress resistance: None tested.
Fruit and seed set: None observed.

COMPARISON WITH PARENTAL AND COMMERCIAL VARIETIES

'KLEPZ10271' differs from the female parent, 'PZ 04 0112', in that 'KLEPZ10271' has greenish white flowers, medium green foliage, and a medium growth habit, while 'PZ 04 0112' has clear white flowers, dark green foliage, and a compact growth habit.

'KLEPZ10271' differs from the male parent, 'KLEP01052' (U.S. Plant Pat. No. 13,202), also known as commercial variety 'Caprivi', in that 'KLEPZ10271' has medium green foliage, while 'KLEP01052' has light green foliage. In addition, 'KLEPZ10271' has larger, round flowers than 'KLEP01052'. Further, 'KLEPZ10271' is tolerant to extreme weather conditions, such as heat and rain, while 'KLEP01052' is not as tolerant to such conditions.

We claim:

1. A new and distinct variety of *Pelargonium* plant named 'KLEPZ10271' as shown and described herein.

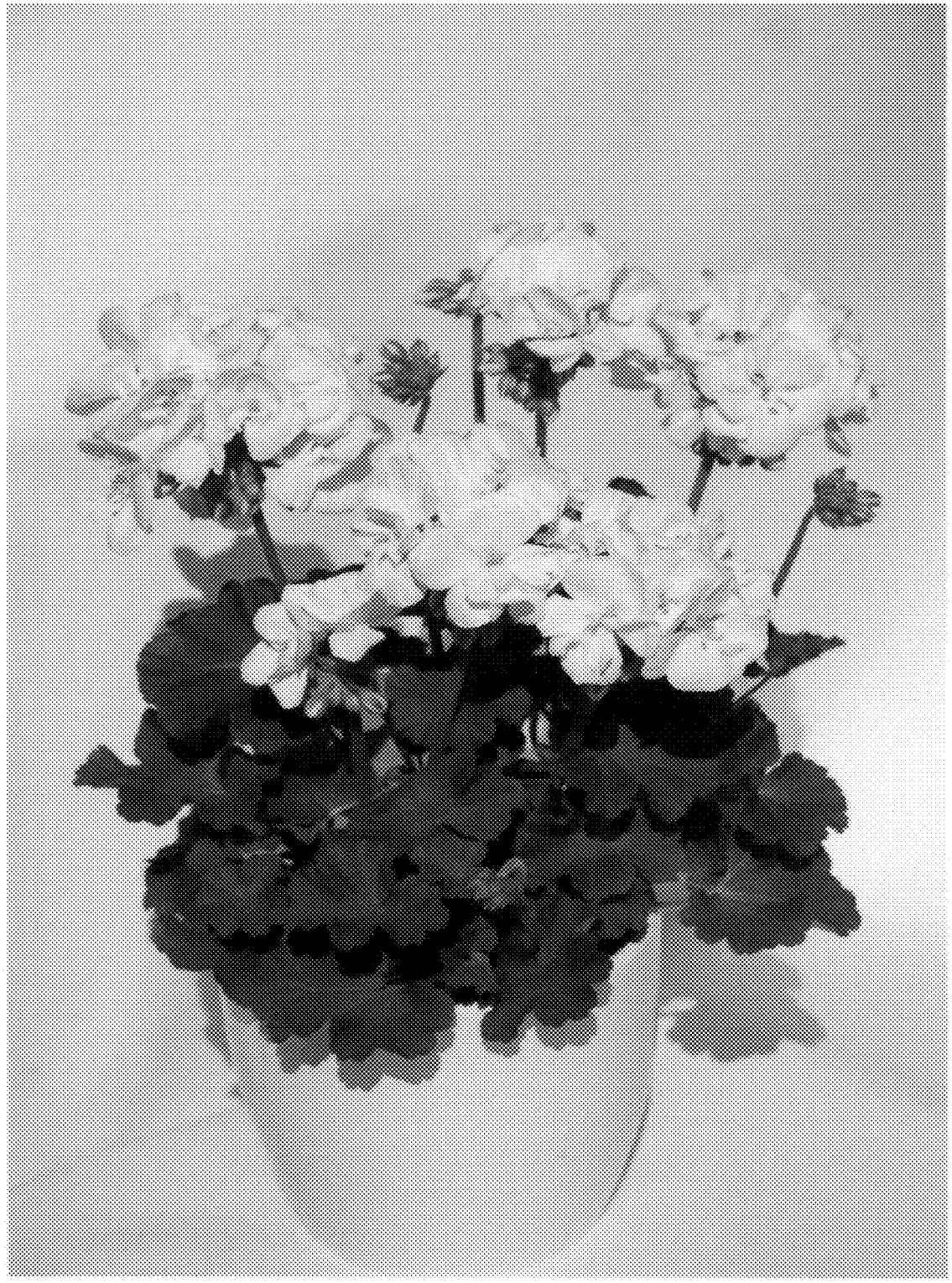

* * * * *